United States Patent [19]

Gunnarsson

[11] Patent Number: 4,758,096

[45] Date of Patent: Jul. 19, 1988

[54] APPARATUS FOR MIXING BONE CEMENT IN VACUUM

[75] Inventor: Kjell Gunnarsson, Höör, Sweden

[73] Assignee: Mit AB, Sjobo, Sweden

[21] Appl. No.: 939,106

[22] Filed: Dec. 8, 1986

[30] Foreign Application Priority Data

Dec. 23, 1985 [SE] Sweden .................... 8506110

[51] Int. Cl.⁴ .............................................. B01F 13/06
[52] U.S. Cl. .................................... 366/139; 366/189; 366/197
[58] Field of Search .................. 366/139, 101–104, 366/163, 191, 189, 190, 197, 203, 602; 222/152; 141/8

[56] References Cited

U.S. PATENT DOCUMENTS

| | | | |
|---|---|---|---|
| 2,696,022 | 12/1954 | Steinbock et al. | 366/139 X |
| 3,131,912 | 5/1964 | Steinbock, Jr. | 366/139 X |
| 3,918,687 | 11/1975 | Hubers et al. | 366/139 |
| 4,185,072 | 1/1980 | Puderbaugh et al. | 366/139 X |
| 4,457,629 | 7/1984 | Liaw et al. | 366/191 X |
| 4,577,973 | 3/1986 | Occelli | 366/139 |
| 4,653,568 | 3/1987 | Baldelli | 366/139 X |

Primary Examiner—John Petrakes
Attorney, Agent, or Firm—Foley & Lardner, Schwartz, Jeffery, Schwaab, Mack, Blumenthal & Evans

[57] ABSTRACT

This invention relates to an apparatus for mixing bone cement in vacuum, in which mixing takes place in a container (11) from which ready-mixed bone cement (4) is adapted to be ejected by means of a piston (2) in the mixing container (1) for supplying the bone cement (4) to a hollow in the bone wherein a prosthesis is to be fixed by means of the bone cement (4), and the mixing container (1) is connectable to a vacuum device which is adapted to generate vacuum in the mixing container (1) during mixing.

With a view to providing an apparatus of simple and compact design, which permits efficient retention of the mixing container during mixing, the vacuum device comprises a vacuum container (9) in which the mixing container (1) is adapted to be disposed in such a way that the mixing container spaces (3, 6) on both sides (5, 7) of the piston (2) communicate with the interior (10) of the vacuum container (9) whereby the same vacuum is obtained on both sides of the piston (2).

10 Claims, 2 Drawing Sheets

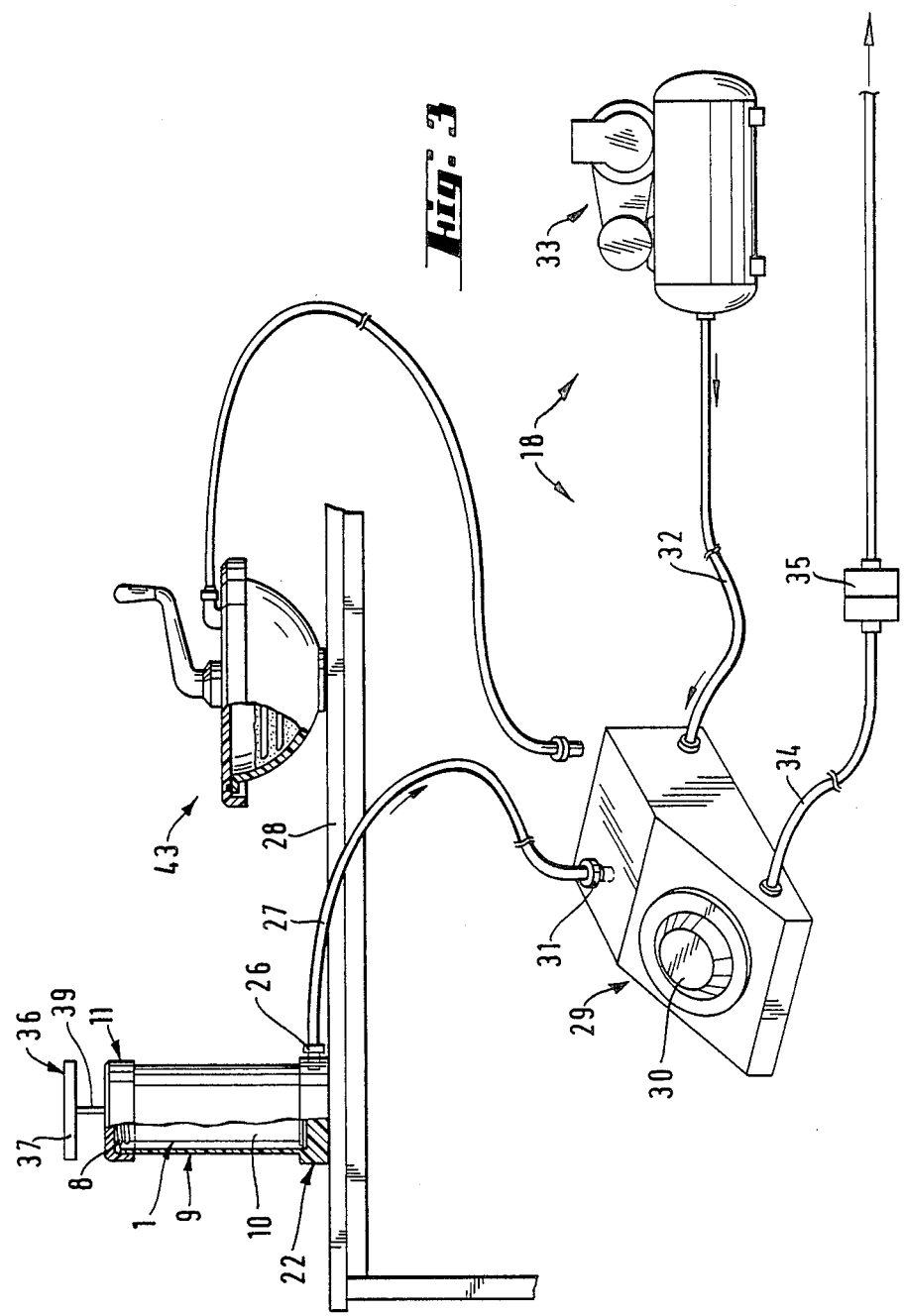

APPARATUS FOR MIXING BONE CEMENT IN VACUUM

BACKGROUND

1. Field of the Invention

This invention relates to an apparatus for mixing bone cement in vacuum, in which mixing takes place in a container from which ready-mixed bone cement is ejected by means of a piston in the mixing container for supplying the bone cement to a hollow in the bone wherein a prosthesis is to be fixed by means of the bone cement, the mixing container being connectable to a vacuum device adapted to generate vacuum in the mixing container during mixing.

2. Related Art

For the generation of vacuum in the space on that side of the mixing container piston which contains bone cement, the mixing container is provided with a cover through which said space is connected to a vacuum device. To avoid unintentional shifting of the piston and resulting compression of the components in the mixing container, by vacuum prevaling on one side of the piston, it has been necessary to manufacture for the mixing container a special base which comprises a coupling for connecting the vacuum device to the space of the mixing container on the opposite side of the piston to create the same pressure below atmospheric on said side as in the space of the mixing container where said components are contained. This implies that the mixing container must be connected at two points to the vacuum device, and furthermore it is difficult to retain the mixing container in sealing position on the base.

SUMMARY

The present invention has for its object to overcome the above-mentioned disadvantages from which the prior-art apparatuses suffer and to provide an apparatus of simple and compact design which permits efficient retention of the mixing container during mixing.

This object is realized by means of the present invention in that the vacuum device comprises a vacuum container in which the mixing container is adapted to be disposed in such a way that the mixing container spaces on both sides of the piston communicate with the interior of the vacuum container whereby the same vacuum is obtained on both sides of the piston.

It is hereby achieved that vacuum is generated on both sides of the piston with the aid of a single vacuum connection and furthermore the mixing container is firmly and steadily retained in position during the mixing operation.

BRIEF DESCRIPTION OF THE DRAWINGS

The above as well as further characteristic features of the invention and the advantages gained thereby will be more fully described in the following, with reference to the accompanying drawings in which:

FIG. 3 is a diagrammatic view showing the connection of the vacuum container to a vacuum source.

DETAILED DESCRIPTION OF THE INVENTION

Figure 1:
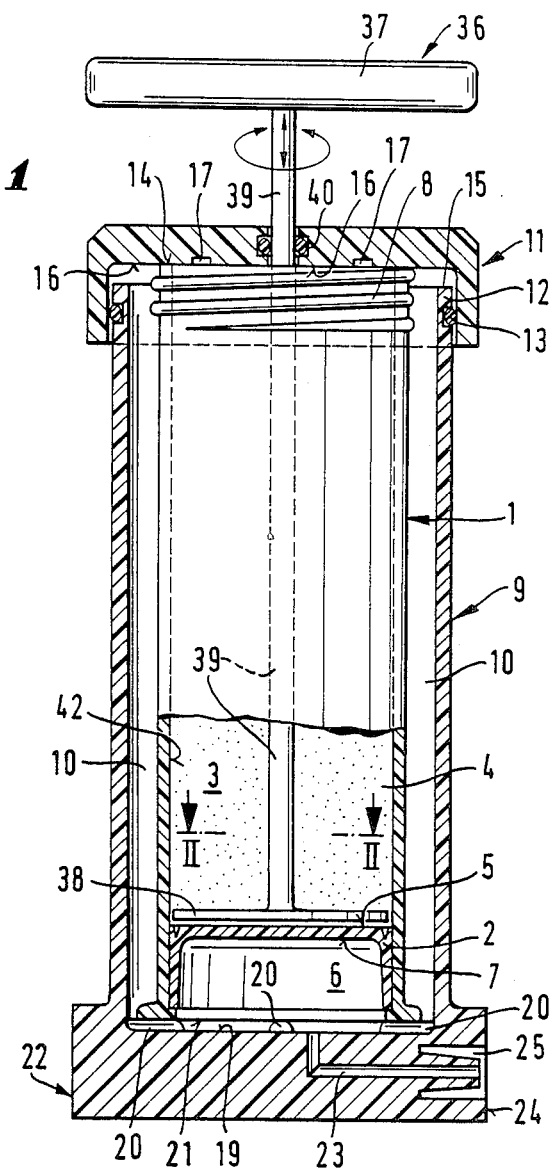
FIG. 1 is a side elevation in cross section of the vacuum container according to the invention with the mixing container disposed therein and with the pertaining agitator.

The present invention thus resides in an apparatus for mixing bone cement in vacuum.

Bone cement is prepared by mixing two or more substances of such properties that the mixture hardens. Of these substances, one preferably is a liquid consisting mainly of monomethylmetacrylate, and another is a powder consisting mainly of polymethylmetacrylate. These and possibly other substances of a suitable nature are mixed and harden into acrylate-based bone cement. However, before this occurs, the mixture has the character of a soft composition which is placed in the bone where a prosthesis is to be inserted. When the composition is in position in the bone, the prosthesis is passed thereinto and fixed in position as the bone cement hardens.

At the mixing of the substances, considerable volumes of air are incorporated with the mixture, and it has proved that the more air the mixture contains, the more the solidity of the finished product deteriorates. To increase the solidity of the finished product, mixing of the various substances is therefore carried out in vacuum, whereby the supply of air to the mixture is minimized.

Mixing takes place in container 1 of plastic or metal having a movable piston 2 therein which divides the interior of the mixing container into a space 3 for bone cement 4 on one side of the piston, preferably the upper side 5, and into another space 6 on the opposite side of the piston, i.e. in the embodiment illustrated, the underside 7. The mixing container 1 here is cylinder-shaped and has a threaded end portion 8 to which there can be screwed a cover provided with a discharge pipe (not shown). For after mixing, the mixing container 1 is placed in a discharge means (not shown) of a known type, which is adapted to extrude the finished bone cement through the discharge pipe by urging the piston 2 towards the discharge pipe. For this operation, the discharge pipe is introduced into a hollow in the bone, in which a prosthesis shall be fixed by means of the bone cement.

The mixing container 1 is connectable to a vacuum device which is adapted to generate vacuum in the mixing container during mixing. For this purpose the vacuum device comprises a vacuum container 9 in which the mixing container 1 is adapted to be disposed in such a way that the mixing container spaces 3 and 6 on both sides 5 and 7 of the piston 2 communicate with the interior 10 of the vacuum container whereby the same vacuum is obtained on both sides of the piston. This will prevent the piston 2 from being displaced in one or the other direction as long as vacuum is maintained in the vacuum container 9, i.e. as long as mixing takes place, and no separate connections for vacuum on the respective sides of the piston are required.

The vacuum container 9 which is likewise made of plastic or metal is closed by means of a cover 11 which is urged by the vacuum against the mixing container 1 to keep it fixed in the vacuum container during the mixing of the bone cement 4. In the illustrated embodiment, the cover 11 surrounds an upper part 12 of the vacuum container 9 and cooperates with said part via a sealing means, preferably an O-ring 13. For fixation of the mixing container 1 the cover bears against an upper end surface 14 of the container. To facilitate fixation of the mixing container 1 in a mixing position in the vacuum container 9, the mixing container in the illustrated embodiment also projects some distance above the rim 15 of the vacuum container, whereby the cover 11 will bear against the end surface of the upwardly projecting part, in this instance the end surface 14 of the threaded end portion 8. With a view to facilitating the creation of vacuum in the space 3 for the bone cement 4 in the mixing container 1, the cover 11 on the inside 16 may preferably have one or more grooves 17 connecting the space 3 with the interior 10 of the vacuum container 19.

To ensure connection between the bone cement receiving space 3 of the mixing container 1 on one side 5 (the upper side) of the piston 2 via the space 10 of the vacuum container 9, which space surrounds the mixing container, and the space 6 of the mixing container on the other, lower, side 7 of the piston as well as the vacuum source 18 of the vacuum device (see FIG. 3), the vacuum container is provided at its bottom 19 with upstanding ribs 20 against which a bottom surface 21 of the mixing container is adapted to bear. For in the bottom 19 of the vacuum container 9 there opens one end of conduit 23 formed in the base portion 22 of the vacuum container, while the other end of said conduit opens in the side 24 of said base portion. In connection with the conduit 23 which opens here, the side surface 24 of the base portion 22 is also formed with a coupling member 25 for an adapter 26 to a conduit 27 for the connection of the vacuum container 9 to the vacuum source 18 (see FIG. 3).

With a view to making sure that the production of bone cement always takes place under substantially sterile conditions, the vacuum container 9 is placed e.g. on a table 28 and is in communication, via the conduit 27 which is sterile like the vacuum container, with a compressed air operated vacuum pump 29 associated with the vacuum source 18 and having a pedal 30 for engaging and disengaging the vacuum device (see FIG. 3). The conduit 27 is connected to the vacuum pump 29 by means of an adapter 31 of a type corresponding to the adapter 26 and is preferably provided at the adapter 31 with a filter (not shown) of conventional design to separate the sterile interior of the vacuum container 9 from the vacuum source. The vacuum pump 29 is disposed on the floor at a distance from the vacuum container 9 and connected via a conduit 32 to a compressor 33 which supplies an ejector means (not shown) in the vacuum pump with compressed air. The ejector means in a known manner generates vacuum in the vacuum container 9 in that air is sucked via the conduit 27 out of the vacuum container and via the ejector means out of the vacuum pump 29 and led into a conduit 34 preferably having a filter 35 and/or being connected to a ventilation system to eliminate the injurious gases arising during the mixing of the bone cement.

Figure 2:
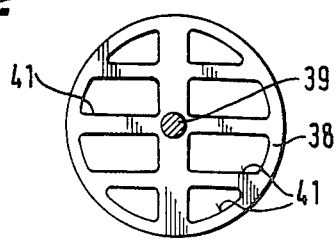
FIG. 2 is a plan view of an embodiment of a mixing element for the agitator of the vacuum container according to FIG. 1.

When a pressure below atmospheric of 0.05–0.5 bar absolute pressure, preferably 0.15 bar absolute pressure (85% vacuum) has been generated, mixing of the substances which are to form the bone cement takes place with the aid of an agitator 36 (FIG. 1) mounted in the cover 11 of the vacuum container 9 and having a handle 37 located outside of the cover for manual operation of the agitator and a mixing element 38 which is arranged to be placed in the space 3 of the mixing container 1 and which is controlled by means of the handle via an operating rod 39 to which the mixing element is welded or soldered. To maintain the vacuum in the vacuum container 9 and the mixing container 1, the operating rod 39 at the lead-in thereof through the cover 11 is surrounded by a sealing means disposed in the cover, such as an O-ring 40. The agitator 36 is both slidably and rotatably mounted in the cover 11 to permit agitation of the bone cement 4 or the substances forming it in that it is removed vertically in the mixing container 1 and/or rotated therein. The mixing element 38 of the agitator 36 is movable between a position close to the piston 2 as in FIG. 1) and a position close to the cover 11. To permit movement of the mixing element 38 between said positions during the mixing procedure and an efficient mixing of the bone cement 4, the mixing element preferably is of planar shape and extends transversely to the longitudinal axis of the mixing container 1 and furthermore has through holes 41 (see FIG. 2) therein to permit bone cement to pass therethrough. Besides the mixing element 38 is of such a design that it bears against or lies in immediate vicinity of the inner side 42 of the mixing container 1 so that upon longitudinal displacement in the mixing container said element will carry along bone cement 4 adhering to the inner side of the mixing container.

Generation of vacuum and mixing of bone cement by means of the apparatus according to the present invention may be summarized as follows:

The substances or components of the bone cement 4 are supplied to the space 3 in the mixing container 1, whereupon the mixing container is placed in the vacuum container 9. The cover 11 is lowered in position over the open upper part 12 of the vacuum container 9. The hose or conduit 27 is connected with the vacuum container 9 and the vacuum source 18 is started so that vacuum is generated both in the space 3 on one side of the piston 2 and in the space 6 below the piston. This will prevent the piston 2 being sucked in an upward direction by the vacuum in the space 3 since an equally large vacuum prevails on the other side of the piston. Said vacuum will also pull the cover 11 into application with the mixing container 1 for the fixation thereof. Mixing can now take place by means of the agitator 36 whose mixing element 38 is moved up and down in the space 3 simultaneously as said element is rotated.

After finished mixing, air is led into the vacuum container 9, the cover 11 with the agitator 36 is removed, the mixing container 1 is taken out of the vacuum container and instead provided with a discharge pipe as described above, the mixing container being then ready for use together with a discharge device of known design. The bone cement mixture 4 need not therefore be moved from one container to another before it is placed in a hollow cavity in a bone.

As will appear from FIG. 3, it is of course obvious that the vacuum source 18 of the vacuum device, which is not a part of the present invention, can be connected to mixing containers of a type other than that described above for mixing bone cement and thus also to mixing containers 43 that are not used later for the discharge of the bone cement.

Moreover, it is obvious to one skilled in the art that the present invention may be modified and changed within the scope of the appendant claims without departing from the invention and the object thereof.

I claim:

1. An apparatus for mixing bone cement in a vacuum comprising:
   (a) a mixing container;
   (b) means on the mixing container for connecting the mixing container to a vacuum source;

(c) a vacuum container surrounding the mixing container;

(d) a piston having an upper side and an underside positioned in the mixing container;

(e) a first space forming a mixing space being formed in the mixing container on the upper side of the piston and a second space being formed on the underside of the piston;

(f) means for communicating the first and second spaces with an interior of the vacuum container, whereby the vacuum is the same on both sides of the piston.

2. Apparatus as claimed in claim 1, characterized in that the vacuum container is closed by a cover arranged to be urged by the vacuum against the mixing container to keep the mixing container fixed in the vacuum container during a bone cement mixing process.

3. Apparatus as claimed in claim 2, characterized in that the cover surrounds an upper part of the vacuum container and cooperates with the upper part via a sealing means and that the cover bears against an upper end surface of the mixing container.

4. Apparatus as claimed in claim 3, characterized in that the mixing container in a mixing position in the vacuum container projects some distance above a rim of the vacuum container and that the cover bears against the end surface of an upwardly projecting part.

5. Apparatus as claimed in claim 1, characterized in that the vacuum container is provided at a bottom with upstanding rib means against which a bottom surface of the mixing container is adapted to bear, thereby ensuring that the vacuum source communicates with the second space on the second side of the piston and via a space in the vacuum container surrounding the mixing container, with the first space of the mixing container on the first side of the piston.

6. Apparatus as claimed in claim 1 characterized in that the vacuum container is closable with the aid of a cover comprising an agitator with a handle located outside of the cover for manual operation of the agitator and with a mixing element in the first space.

7. Apparatus as claimed in claim 6, characterized in that the agitator is both slidably and rotatably mounted in the cover to permit agitation of the bone cement in that it is moved vertically in the mixing container or rotated therein.

8. Apparatus as claimed in claim 7, characterized in that the agitator extending transverse to the longitudinal axis of the mixing container the mixing element having through holes therein to permit bone cement to pass therethrough.

9. Apparatus as claimed in claim 7 characterized in that the agitator is movable in the mixing container so as to enable shifting of a mixing element thereof between a position close to the piston and a position close to the cover.

10. Apparatus as claimed in claim 7, characterized in that the agitator has a mixing element which at least lies in immediate vicinity of an inner side of the mixing container so that upon longitudinal displacement in the mixing container the mixing element will carry along bone cement adhering to an inner side of the mixing container.

* * * * *